US011235017B2

(12) United States Patent
Alimonti et al.

(10) Patent No.: US 11,235,017 B2
(45) Date of Patent: *Feb. 1, 2022

(54) USE OF A VEGETABLE EXTRACT AS AN ACTIVE AGENT IN THE TREATMENT OF DERMATOLOGICAL DISEASES

(71) Applicant: Altergon SA, Lugano (CH)

(72) Inventors: Andrea Alimonti, Lugano (CH); Andrea Maria Giori, Lugano (CH); Monica Montopoli, Lugano (CH); Jessica Cadau, Lugano (CH)

(73) Assignee: Altergon SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/955,280

(22) PCT Filed: Dec. 14, 2018

(86) PCT No.: PCT/EP2018/085073
§ 371 (c)(1),
(2) Date: Jun. 18, 2020

(87) PCT Pub. No.: WO2019/121427
PCT Pub. Date: Jun. 27, 2019

(65) Prior Publication Data
US 2020/0376065 A1    Dec. 3, 2020

(30) Foreign Application Priority Data

Dec. 19, 2017 (IT) .................... 102017000146677

(51) Int. Cl.
*A61K 36/537* (2006.01)
*A61P 17/00* (2006.01)
*A61K 9/00* (2006.01)

(52) U.S. Cl.
CPC .......... *A61K 36/537* (2013.01); *A61K 9/0014* (2013.01); *A61P 17/00* (2018.01)

(58) Field of Classification Search
None
See application file for complete search history.

(56) References Cited

U.S. PATENT DOCUMENTS 3,969,516 A * 7/1976 Stoughton ............. A61K 8/602
514/24

FOREIGN PATENT DOCUMENTS

EP    2762131 A1 *  8/2014  ........... A61K 8/9789
EP    2762131 A1    8/2014

OTHER PUBLICATIONS

Almanza G., et al., "Clerodane diterpenoids and an ursane triterpenoid from Salvia haenkei. Computer-assisted structural elucidation", Tetrahedron, vol. 53, No. 43, Oct. 27, 1997, pp. 14719-14728.

(Continued)

*Primary Examiner* — Melissa S Mercier
(74) *Attorney, Agent, or Firm* — Silvia Salvadori, P.C.; Silvia Salvadori

(57) ABSTRACT

The use of *Salvia haenkei* extract as an active agent in the treatment of dermatological diseases is described. Also described are pharmaceutical compositions comprising *Salvia haenkei* extract and suitable pharmaceutically acceptable excipients, for use in the treatment of dermatological diseases.

10 Claims, 6 Drawing Sheets

(56) References Cited

OTHER PUBLICATIONS

Evert T. et al., "The relationship between plant use and plant diversity in the Bolivian andes, with special reference to medicinal plant use", Human Ecology, vol. 36, No. 6, Dec. 6, 2008, pp. 861-879.
Fournet A. et al., "Leishmanicidal and trypanocidal activities of Bolivian medicinal plants", Journal of Ethnopharmacology, vol. 41, No. 1-2, Jan. 1, 1994, pp. 19-37.
International Search Report and Written Opinion of PCT/EP2018/085073 dated Apr. 3, 2019.
Matic I., et al., "Identification of "Salvia haenkei" as gerosuppressant agent by using an integrated senescence-screening assay", Aging, vol. 8, No. 12, Dec. 28, 2016, pp. 3223-3240.
Topcu G. "Bioactive triterpenoids from *Salvia* species", Journal of Natural Produ, American Chemical Society, US, vol. 69, No. 3, Mar. 9, 2006, pp. 482-487.

* cited by examiner 0,01 µM UVB 0,1 µM 0,1 µM UVB

USE OF A VEGETABLE EXTRACT AS AN ACTIVE AGENT IN THE TREATMENT OF DERMATOLOGICAL DISEASES

This application is a U.S. national stage of PCT/IB2018/085073 filed on 14 Dec. 2018, which claims priority to and the benefit of Italian Application No. 102017000146677 filed on 19 Dec. 2017, the contents of which are incorporated herein by reference in their entireties.

FIELD OF THE INVENTION

The present invention relates to the use of *Salvia haenkei* extract as an active agent in the treatment of dermatological diseases, being able to offer a significant contribution in tissue regeneration. Furthermore, the present invention also relates to a pharmaceutical composition comprising *Salvia haenkei* extract and suitable pharmaceutically acceptable excipients, for use in the treatment of dermatological diseases.

BACKGROUND ART

Numerous skin disorders cause hypertrophy of the horny layer of the epidermis, an event also known as hyperkeratinization. The thickened superficial layer of the epidermis generates the formation of scaly-like plaques on the surface of the skin. These plaques are a common manifestation of a series of disorders called ichthyosis due to their similarity with fish scales. The plaques may be symptoms of a disorder coming from underlying layers of the skin, but once formed the plaques themselves hinder the topical treatment of the disorder that caused them. Furthermore, the hypertrophic skin layer may also contain itself infections therewithin.

Typical examples of ichthyosis that have no completely clear etiologies include psoriasis, pityriasis rosea of Gibert, rosacea and seborrheic dermatitis. These disorders are typically treated symptomatically with keratolytes agents to remove plaques and with glucocorticoids to relieve inflammation. Dermaphitosis is ichthyosis caused by fungal infections. The hyphae and the spores are confined to non-viable tissue portions and then proliferate in the hyperchratinised tissues of skin, hair and nails. Examples of typical dermaphitosis include *tinea capitis, tinea pedis* (athlete's foot), *tinea faciei, tinea corporis* and *tinea unguium*. These disorders are treated with antifungal agents and topically with keratolytes agents to remove the horny and infected layer.

Skin disorders can also be caused by hormonal imbalance. This imbalance can cause testosterone levels to rise, as in the puberty phase. Testosterone is reduced to dihydrotestosterone (DHT) in the target tissues, including the sebaceous glands. In the common dermatological disorder of acne, DHT binds to receptors in the pilosebaceous complex and stimulates excessive secretion of sebum. The sebum acts as a nutrient for bacteria such as *Propionibacterium acnes*, which infect the sebaceous gland and lead to an inflammatory response and abnormal crowning of the skin. Acne is typically treated with antibacterial and antiseptic agents and also with keratolyte agents, such as salicylic acid or retinoic acid, to remove hyperkeratinized tissue.

The terms eczema and dermatitis are instead generally used to indicate a severe inflammation of the skin, typically accompanied by redness, swelling, oozing, scaling and itching. Eczema can take the form of contact dermatitis or atopic dermatitis in people "atopic" or allergic by nature. If the scalp is involved the disorder is known as seborrheic dermatitis. Dermatitis can be caused by chemicals, plants, clothing fabrics, metallic materials and even medicines.

Atopic dermatitis is a chronic or chronic-relapsing eczema caused by immunological and non-immunological factors. The former consist of food allergens, inhalants or contact, the latter of external irritants, infections, neurovegetative disorders, disorders of lipid metabolism, sweating and stress. Atopic dermatitis is characterized by a reduction in the epidermal ceramides which leads to a weakening of the barrier function of the skin, increased irritability and an increase in transepidermal water loss which can increase if an epidermal inflammatory condition coexists. This facilitates the penetration into the skin of allergens and haptens that bind to keratinocytes and Langerhans cells, activating them. Skin affected by dermatitis is more susceptible to infections due to elevated levels of inflammatory cytokines such as IL-4 or IL-13.

Skin disorders, such as those described above, can be treated with known drugs, however, it is important to keep in mind that sometimes the drugs themselves are the cause of skin reactions and that their use should however be as limited as possible.

The object of the present invention is therefore to find an effective remedy for the treatment of dermatological diseases, which is also well tolerated by the body and which can also be used for long periods having minimized side effects.

SUMMARY OF THE INVENTION

Said object has been achieved by the use of *Salvia haenkei* extract as an active agent in the treatment of dermatological diseases, as reported in 1.

In another aspect, the present invention relates to a pharmaceutical composition comprising *Salvia haenkei* extract and suitable pharmaceutically acceptable excipients, for use in the treatment of dermatological diseases.

For the purposes of the present invention, said dermatological diseases are ichthyosis, excessive secretion of sebum, microbial infection, dermatophytosis, acne, psoriasis, seborrheic dermatitis, rosacea, dandruff, alopecia, allergic dermatosis, urticaria, scleroderma, contact dermatitis, atopic dermatitis, chronic actinic dermatitis, photodermatosis.

In another aspect, the present invention relates to a pharmaceutical composition comprising *Salvia haenkei* extract and at least one active dermatological ingredient selected from anti-inflammatory agents, cortisonic agents, antibiotics, antihistaminic agents, anti-acne agents, antidandruff agents, anti-psoriasis agents, antifungal agents, antibacterial agents, anti-seborrheic agents, keratolytic agents, humectants, anti-free radical agents, antioxidants, vitamins, and mixtures thereof.

BRIEF DESCRIPTION OF THE FIGURES

The characteristics and the advantages of the present invention will become clear from the following detailed description, the working examples provided for illustrative purposes and the accompanying figures, wherein.

DETAILED DESCRIPTION OF THE INVENTION

Figure 1A:
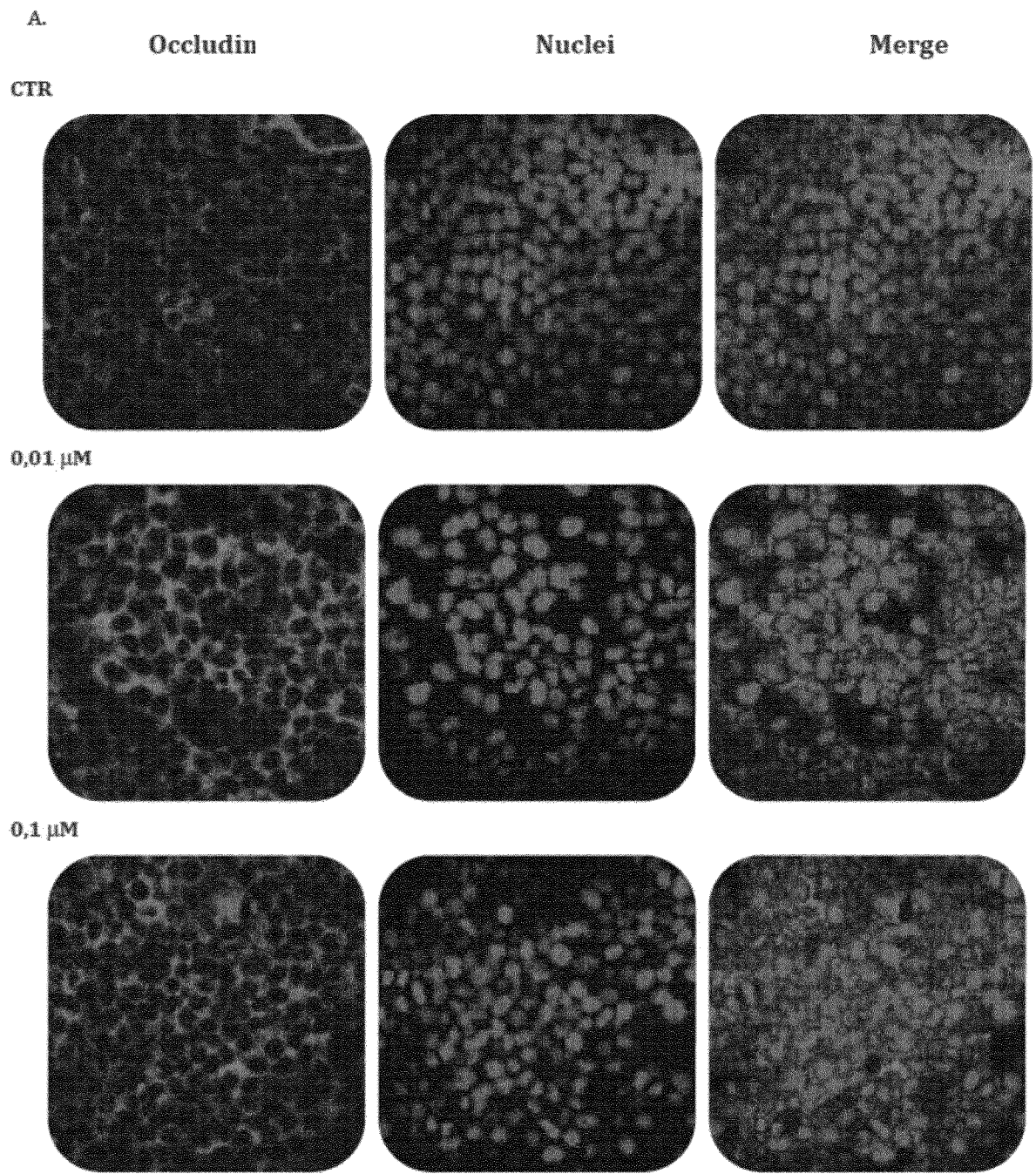
FIG. 1 shows the effect of *Salvia haenkei* 0.1 and 0.01 µM (SH01) on the expression of occludin in HaCaT keratinocytes before (FIG. 1A) and after (FIG. 1B) exposure to UVB ultraviolet radiation 30 KJ/m$^2$. Occludin markings (Alexa Fluor 488λ etc.=490 nm λ emis=525 nm) and nuclei (propidium iodide λ max etc.=495 nm; λ max emis=610 nm)

*Salvia haenkei* is a shrub coming from Bolivia and Peru, and although it is commonly called "prawn sage" due to the color and shape of its shrimp-like flowers, its scientific name dates from the era of Spanish exploration of the Americas at the end of the eighteenth century. Morphologically, it is characterized by lance-shaped leaves with dentate margins whose length exceeds 12 cm. Their color is light green and the surface is wrinkled. The inflorescence is very long, over 20 cm and is defined as "raceme", i.e. the flowers are inserted at the level of the central axis through the peduncles of the same length at different heights along the same flower axis.

For the preparation of the extract, the aerial parts of the plant are generally used, i.e. stem, leaves, flowers or mixtures thereof. These parts can be used fresh or after drying under controlled conditions. In both cases, the individual parts or mixtures thereof are contacted with a suitable extraction solvent, by using conventional extraction methods, such as maceration or percolation, or more complex techniques, such as for example extraction with ultrasound, microwaves, pressure or supercritical fluids.

After separation of the exhausted plant, the extract can be used as such, or after substitution of the extractive solvent with one more suitable for human use (such as glycerine or glycol, if not used in the extraction phase). Preferably, the extracting solvent is removed to give a dry extract. For the removal of the extractive solvent, the preferred techniques are evaporation at reduced pressure and low temperature, and atomization.

The extract can also be subjected to subsequent purification steps, to remove potential contaminants (such as lipophilic pesticides), impurities (such as chlorophyll) or to increase the concentration of secondary metabolites.

The dry extract can be added with suitable excipients, for example to make it smoother, less hygroscopic or standardized in the content of secondary metabolites. Among the excipients that can be used are, for example, silica, maltodextrins, microcrystalline cellulose.

Among the solvents suitable for the preparation of *Salvia haenkei* extract, those with a medium polarity are preferably selected, as being capable of effectively extracting the secondary metabolites of the plant. Preferably, such extraction solvents have dielectric constant of 8 to 60. The so obtained *Salvia haenkei* extract contains a pool of terpenoid compounds, in particular diterpenoids and triterpenoids (Almanza, G. et al., (1997) Clerodane diterpenoids and an ursane triterpenoid from *Salvia haenkei* Computer-assisted structural elucidation, Tetrahedron, 53 (43), pp. 14719-14728), as well as gallic acid and its derivatives, and chlorogenic acid and its derivatives. Some of these compounds are specific to this species of *Salvia* and differentiate it from other species of the same genus, contributing reasonably to the characteristic activity of its extracts.

Examples of usable extraction solvents are alcohols having up to 4 carbon atoms, including diols and triols, aldehydes, ketones, organic esters, chlorinated compounds, and mixtures thereof. When miscible, such solvents can also be used in mixture with water.

Preferred solvents include methanol, ethanol, isopropanol, butanol, ethylene glycol, propylene glycol, glycerol, acetone, ethyl acetate and mixtures thereof, as such or mixed with water.

In preferred embodiments, said extraction solvent is a water-alcohol solution, even more preferably it is a 40-80% alcohol solution. Said alcohol is preferably methanol or ethanol. Embodiments in which the extraction solvent is a 60-80% ethanol solution are particularly preferred.

Preferably, the preparation of said *Salvia haenkei* extract comprises the steps of:
1. collecting aerial parts of *Salvia haenkei*,
2. extracting with a solvent,
3. separating the plant exhausted from the liquid extract, and
4. removing the solvent to give the dry extract.

The aerial parts of step 1. may be fresh or preliminarily dried. If the aerial parts are fresh, just harvested, the greater amount of water physiologically present in the plant shall be taken into account.

The invention therefore relates to the use of *Salvia haenkei* extract as a re-epithelizing agent in the treatment of dermatological diseases.

Said dermatological diseases are ichthyosis, excessive secretion of sebum, microbial infection, dermatophytosis, acne, psoriasis, seborrheic dermatitis, rosacea, dandruff, alopecia, allergic dermatosis, urticaria, scleroderma, contact dermatitis, atopic dermatitis, chronic actinic dermatitis, photodermatosis.

Preferably, said dermatological disease is ichthyosis.

Preferably, said dermatological disease is atopic dermatitis.

In the Examples provided below, markers of protection activity against external stress events, such as filaggrin, were evaluated. Filaggrin is a protein implicated in important physiological functions contributing to homeostasis and to the formation of the skin barrier, but not only. Advanced molecular biology techniques and the use of genetically modified animal models have clarified the multiple roles that filaggrin plays in the physiology of skin, among them, the maintenance of normal flora and the prevention of damage caused by exposure to ultraviolet radiation. In addition to binding the keratin fibers by bonding them together, giving resistance to the skin, its osmotically active peptide derivatives contribute to the formation of the NMF which controls the fundamental balance for the functionality and well-being of the skin. Instead, the trans-UCA (trans-urocanic), chromophore derivative located in the stratum corneum of the human epidermis that absorbs in the ultraviolet making the filaggrin a natural UV filter is phosfo-isomerized to cis-UCA in the presence of UV-B radiation the which is a powerful immunosuppressant (to avoid excessive reactions against cells damaged by radiation under normal exposure conditions) which in the long run is also involved in the pathogenesis processes of skin cancers induced by UV radiation, pH regulator and antimicrobial. The data obtained by immunocytochemistry demonstrate that the *Salvia haenkei* extract is capable of inducing an increase in the expression of filaggrin in keratinocytic level, clearly indicating the efficacy of the extract in the maintenance of cutaneous function.

The variation of occludin expression in keratinocytes, an integral membrane protein involved in tight junction formation along the cell margin, was also evaluated. At the same time, the effect of *Salvia haenkei* on cells exposed to ultraviolet radiation was evaluated, which leads to damage to the junctions and therefore to the integrity of the epidermal layer. What has been seen by immunofluorescence is the increase of occludin expression both in basal conditions and in stress conditions. There was therefore further confirmation that the *Salvia haenkei* extract promotes the process of cell differentiation but above all the maintenance of the barrier integrity.

The keratinocytes interact with each other also through the adherent joints, for this reason it was proceeded with the evaluation of the expression of β catenin, a protein that stabilizes these joints by making a bridge between the cytoskeleton and the surface caderins E. Moreover, having considered UVB as a stressful factor for cells, cells were exposed in parallel to UVB radiation. In fact, when keratinocytes are exposed to UVB radiation, it is known that β catenin is released from the membrane and can move into the nucleus taking part in the WNT pathway, inducing hyperproliferation, differentiation and cell survival, but in this respect the extract does not seem to have details even if probably it is necessary to increase the setting up of the irradiation protocol. The data obtained by immunocytochemistry show that the extract of *Salvia haenkei* increases the expression of β catenin at the cytoplasmic membrane level to indicate a greater ability to maintain the epithelial barrier intact, and if these data are contextualized with those obtained by occludin, it can no doubt confirm that the *Salvia haenkei* extract has the ability to keep the epithelial barrier more intact, thus giving further confirmation of protection. The maintenance of the epithelial barrier plays a fundamental role in many dermatological diseases. This barrier function is mainly exerted by the stratum corneum, the most superficial layer of the skin, and also by the cell-cell junctions and by the proteins associated to the cytoskeleton that give structural solidity. The stratum corneum is not a completely inert covering, in fact it is a semipermeable membrane that acts as a biosensor both for protection against potential environmental elements and for maintaining the physiological and dynamic water balance because it allows the younger cells to replace the old ones that have reached the terminal differentiation. The barrier properties of the stratum corneum also extend to its ability to defend the organism from damage induced by exposure to ultraviolet (UV) radiation and oxidizing agents. When everything works best, the epidermal barrier allows the percutaneous absorption of water and other essential nutrients by blocking the entry to substances instead recognized as harmful, or to infectious agents, thanks to the highly specialized structure.

Taken together, all these data clearly and firmly support that the *Salvia haenkei* extract has the ability to maintain and promote the integrity of the epithelial barrier even under conditions of stress from UVB rays, clarifying its role as a re-epithelizing agent in the treatment of dermatological diseases.

Preferably, said extract is to be administered via topical route, more preferably via external topical, sub-cutaneous topical, mucosal topical, gingival topical, intravesical topical, vaginal topical, rectal topical, or ocular topical route.

Preferably, said extract is to be administered in a dose of 0.1-1500 mg per day.

In preferred embodiments, said extract is to be administered via external topical route in a dose of 1-1000 mg per day, the effective dosage being a function of the extent and severity of the dermatological disease to be treated.

In another aspect, the present invention relates to a pharmaceutical composition comprising *Salvia haenkei* extract and pharmaceutically acceptable carriers, for use in the treatment of dermatological diseases.

Said pharmaceutical composition can be administered via topical route.

Preferably, said pharmaceutical composition is to be administered via external topical, sub-cutaneous topical, mucosal topical, gingival topical, intravesical topical, vaginal topical, rectal topical, or ocular topical route.

In preferred embodiments, said composition is to be administered via external topical route.

Preferably, the pharmaceutical composition comprises *Salvia haenkei* extract in a concentration of 0.1-500 mg/ml of composition, more preferably 1-100 mg/ml.

Said pharmaceutical composition may be in the form of ointment, lotion, cream, emulsion, paste, gel, aqueous solution, spray, patch, serum, soaked gauze, dressing, or a combination thereof.

Said pharmaceutically acceptable vehicles can be rheological additives, buffering agents, antimicrobial agents, antioxidant agents, anti-isothermal agents, antistatic agents, absorbent agents, UV absorbing agents, astringent agents, chelating agents, skin conditioning agents, preservative agents, covering agents, denaturing agents, depigmenting agents, emulsifying agents, film-forming agents, gelling agents, moisturizing agents, hydrotropic agents, binders, soothing agents, smoothing agents, opacifying agents, plasticizing agents, propelling agents, skin protecting agents, reducing agents, cooling agents, sebum-restoring agents, solvents, stabilizing agents, emulsifying stabilizing agents, toning agents, wetting agents, volumizing agents or combinations thereof.

In some embodiments, the pharmaceutical composition for use in the treatment of dermatological diseases further comprises at least one active dermatological principle selected from anti-inflammatory agents, cortisones, antibiotics, antihistamines, anti-acne, anti-dandruff, anti-psoriasis, antifungals, antibacterial, anti-isothermal, keratolytic, humectant, anti-free radicals, antioxidants, vitamins, and their mixtures.

Examples of antifungal agents are econazole and miconazole.

Examples of antibacterial agents are chlorquinol, hexchlorophene, 2,4,4'-trichloro-2'-hydroxybiphenyl ether and usnic acid.

An example of an anti-dandruff agent is ketoconazole.

Examples of anti-isothermal agents are some fatty substances and thiossolone.

Examples of anti-acne agents are retinoic acid and its derivatives.

An example of a keratolytic agent is salicylic acid.

An example of an anti-psoriasis agent is antraline.

All the pharmaceutical compositions described above can be prepared by methods known in the pharmaceutical technique.

It should be understood that all the aspects identified as preferred and advantageous for the *Salvia haenkei* extract are to be deemed as similarly preferred and advantageous also for the pharmaceutical compositions and uses thereof.

It should be also understood that all the combinations of preferred aspects of the *Salvia haenkei* extract of the invention, as well as of the pharmaceutical compositions and uses of the same, as above reported, are to be deemed as hereby disclosed.

Below are working examples of the present invention provided for illustrative purposes.

EXAMPLES

Example 1

Preparation of *Salvia haenkei* Extracts 10 kg of aerial parts of *Salvia haenkei* are harvested from field crops, which are then subjected to a drying process in a ventilated dryer under controlled conditions.

In this way, 1.95 kg of dried plant are obtained, which are minced into a bladed mill to give dried and ground *Salvia haenkei*.

This is used as raw material for the subsequent solvent extraction tests carried out as described below:

1. 100 g of dried and ground *Salvia haenkei* are introduced into a static percolator and covered completely with 200 ml of a water and ethanol 30-70% v/v mixture. It is left to stand for 2 hours and the extraction solvent (170 ml) is recovered from the bottom of the percolator, which is set aside (extract 1);
2. the humid plant left in the percolator is covered with a new 70% aqueous ethanol (170 ml) aliquot, leaving it to rest for 2 hours. The solvent is recovered (165 ml—extract 2);
3. the extraction described in point 2 is repeated until the dry residue of the extract recovered is less than 5% of the total dry residue extracted up to that moment. At that point, the extraction is considered completed and the spent moist plant is eliminated. 6 extractions are required;
4. the extracts obtained from the individual extraction steps (from extract 1 to extract 6) are combined, filtered and concentrated in a rotary evaporator under vacuum, at a low temperature. It is proceeded until a concentrated, viscous solution (35 ml) is obtained;
5. the concentrated extract is transferred to a steel tray and inserted into a under vacuum cabinet dryer, with heating set at 30° C. After 12 hours, the solvent is completely removed (extract weight loss less than 10%, i.e. dry residue higher than 90%). 14.3 g of integral dry extract are obtained. The ratio drug:extract (DER) is 7:1 (extract 1A).
6. the dried extract obtained is added with 10 g of maltodextrin (DE 10) to improve its consistency and the mixture is milled and sieved, thus obtaining 23.7 g of ground dry extract.

By applying the same procedure but different extracting solvents different native dry extracts were prepared.

The table summarizes the results of the various extraction tests:

| extract | extraction solvent | DER |
|---------|-------------------|------|
| 1A | ethanol:water 70:30 | 7:1 |
| 1B | ethanol:water 95:5 | 9.5:1 |
| 1C | acetone | 11:1 |
| 1D | methanol | 8:1 |

| extract | extraction solvent | DER |
|---------|-------------------|------|
| 1E | ethyl acetate | 15:1 |
| 1F | water | 5:1 |
| 1G | methanol:water 50:50 | 6:1 |

In the following Examples, a hydroalcoholic extract of *Salvia haenkei* of Example 1A was used, briefly referred to as "SH01".

Example 2

Qualitative Evaluation of Occludin Expression

The effect of *Salvia haenkei* on the occludin membrane protein was evaluated by immunocytochemistry, which is important for the formation of cellular junctions and therefore the formation and maintenance of the epidermal barrier monolayer. The effect of the extract on exposed cells and not the ultraviolet radiation known for its ability to damage the skin barrier was evaluated.

In FIG. 1A the slides prepared with HaCaT cells not exposed to UVB ultraviolet radiation are reported. It can be seen that already under basal conditions the cells exposed to treatment with SH01 have a higher expression of occludin thus favoring the formation of cellular junctions important for the maintenance of the integrity of the epidermis. In cells exposed to ultraviolet radiation it can be seen how the cells have an altered and no longer well-defined cell margin. In the cells exposed to the treatment with the SH01 extract, on the other hand, it is clear how the margin delimited by the occludin is preserved intact, confirming the activity of this extract on the formation and maintenance of cellular joints.

Figure 1B:
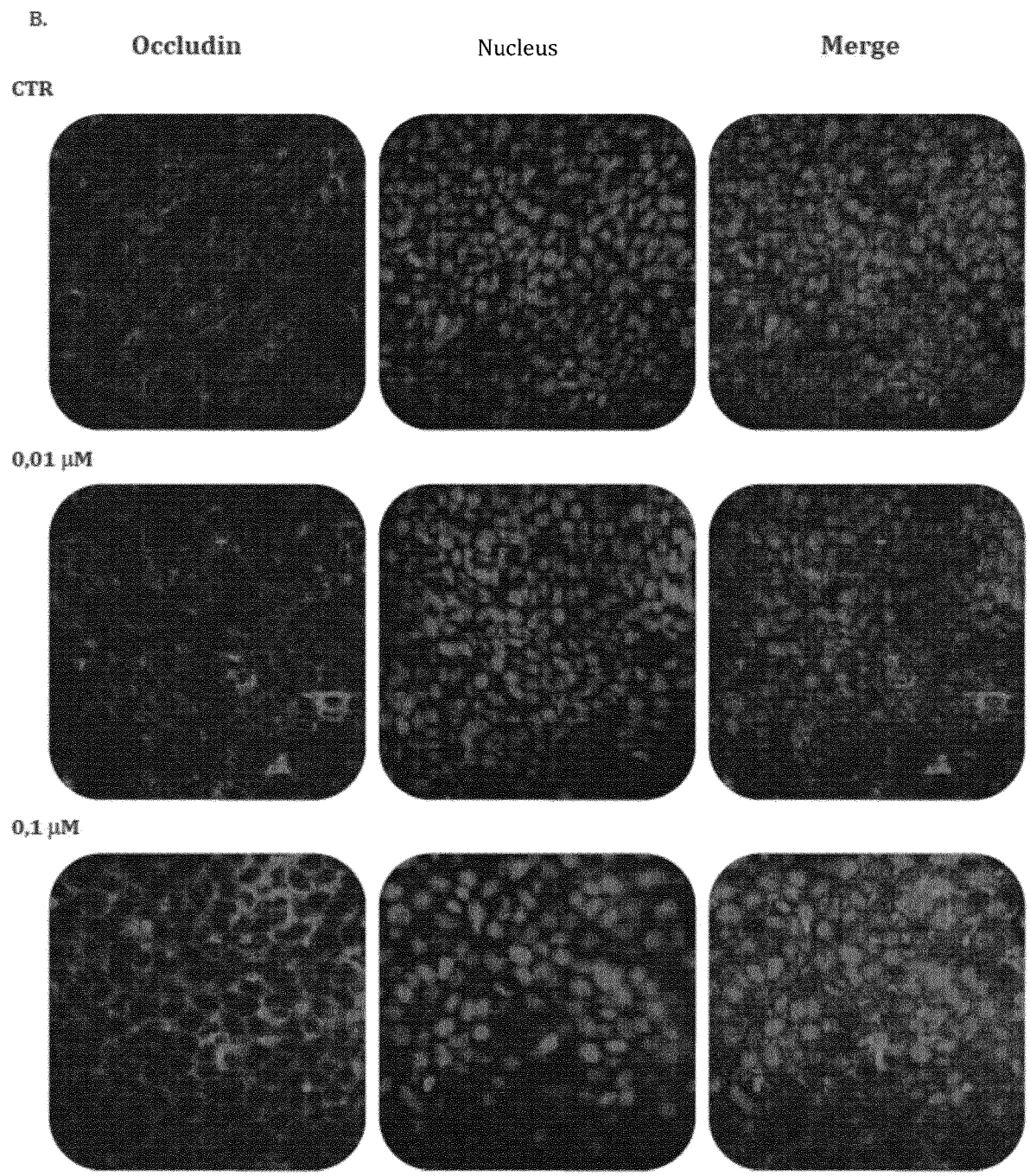

In FIG. 1B the slides prepared with HaCaT cells exposed to UVB are shown where the control slide has a more sparse and less intense expression of occludin whereas in the presence of the occludin treatment it is more intense and borders the cell margin well.

Example 3

Qualitative Analysis of the Expression of Filaggrin

Immunocytochemistry has evaluated the variation in the expression of filaggrin in HaCaT cells, a cytoplasmic protein present in keratinocytes of the stratum corneum which is fundamental for maintaining the barrier function of the skin. The partial or total loss of filaggrin expression, its functional and structural alterations, are the pathogenetic factors responsible for various epidermal dysfunctions.

The expression and localization of filaggrin and actin were visualized by confocal microscopy.

Figure 2A:
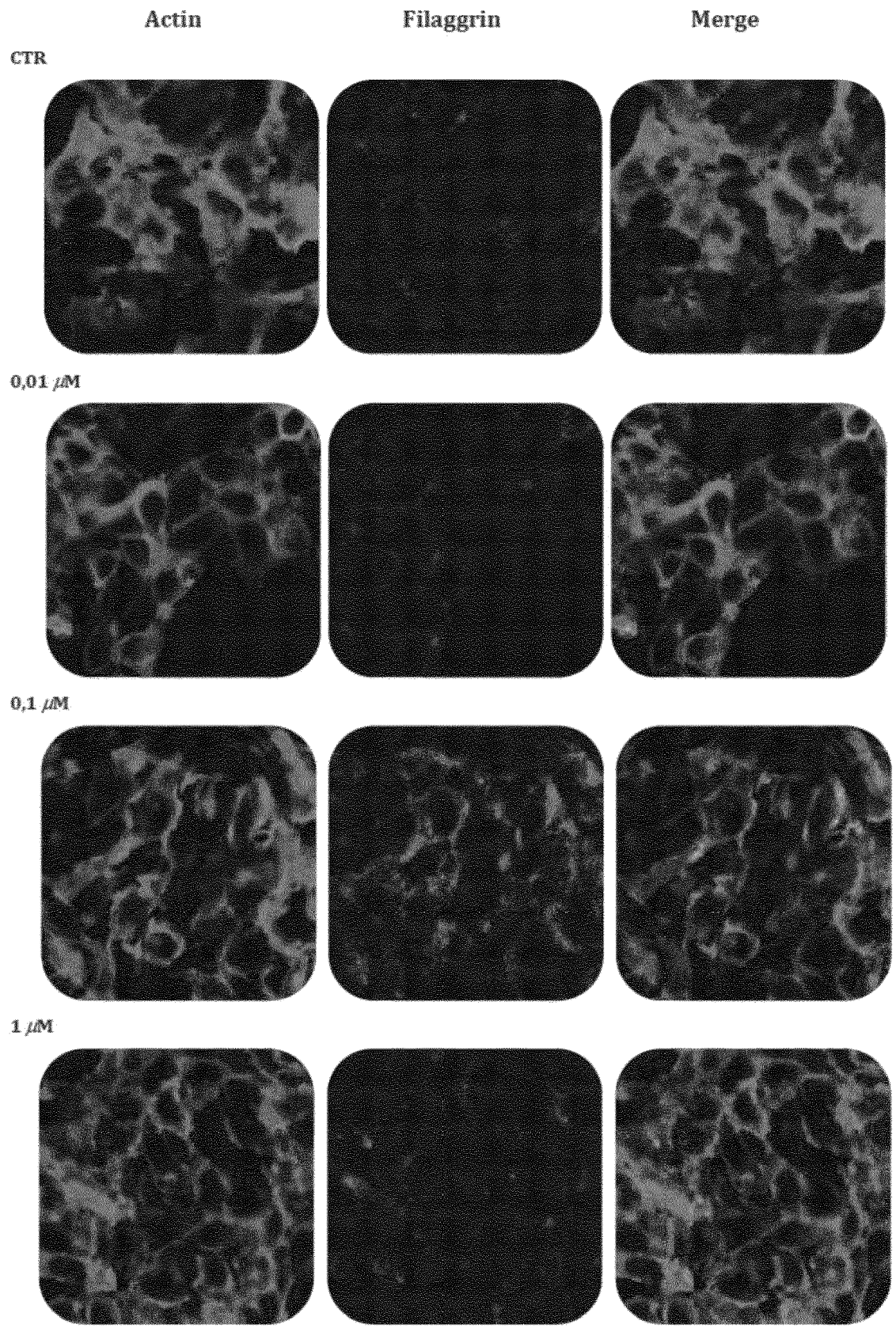
FIG. 2A shows HaCaT cells treated for 24 hours with *Salvia haenkei* 0.01 µM, 0.1 µM, 1 µM (SH01). Filaggrin marking (λ etc=490 nm; λ emis=525 nm) and phalloidin (λ etc=556 nm; λ emis=570 nm). Acquisition with LSM 800 co-operative microscope and ZEN 2.1 software with 60× objective.
Figure 2B:
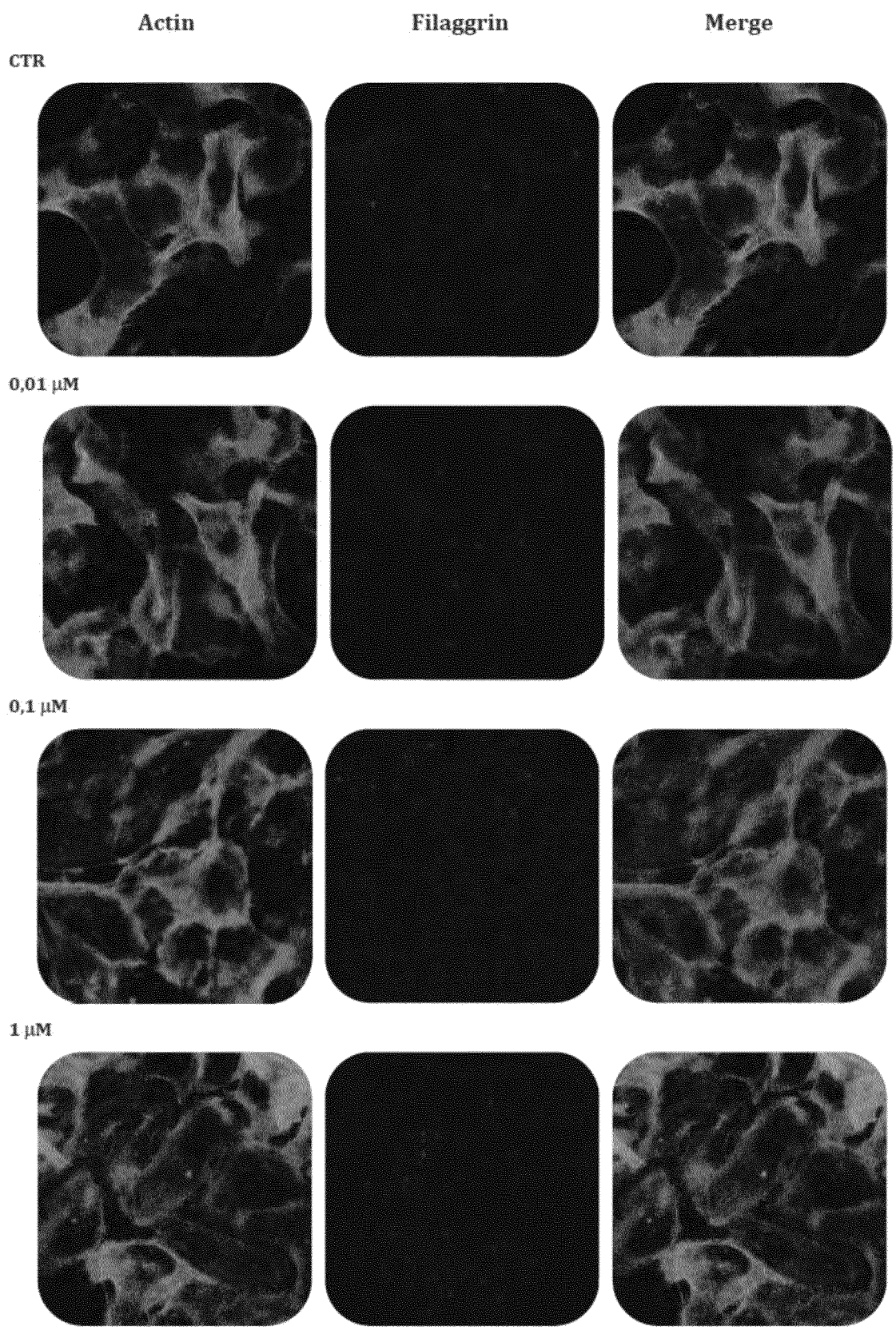
FIG. 2B shows HaCaT cells treated for 24 hours with *Salvia haenkei* 0.01 μM, 0.1 μM, 1 μM (SH01). Filaggrin marking (Alexia Fluor 488, λ etc=490 nm; λ emis=525 nm) and actin (phalloidin, λ etc=556 nm; λ emis=570 nm). Acquisition with LSM 800 co-operative microscope and ZEN 2.1 software with 60× objective.

As shown in FIG. 2A, the labeled filaggrin is expressed at the basal level. This expression increases after 24 hours treatment with SH01 in a concentration-dependent manner. In parallel, observing the expression of F-actin in FIG. 2B, it is possible to observe how the cells arrange the protein in an orderly manner, creating a structural continuity.

Example 4

Evaluation of the Effects on β Catenin

Figure 3A:
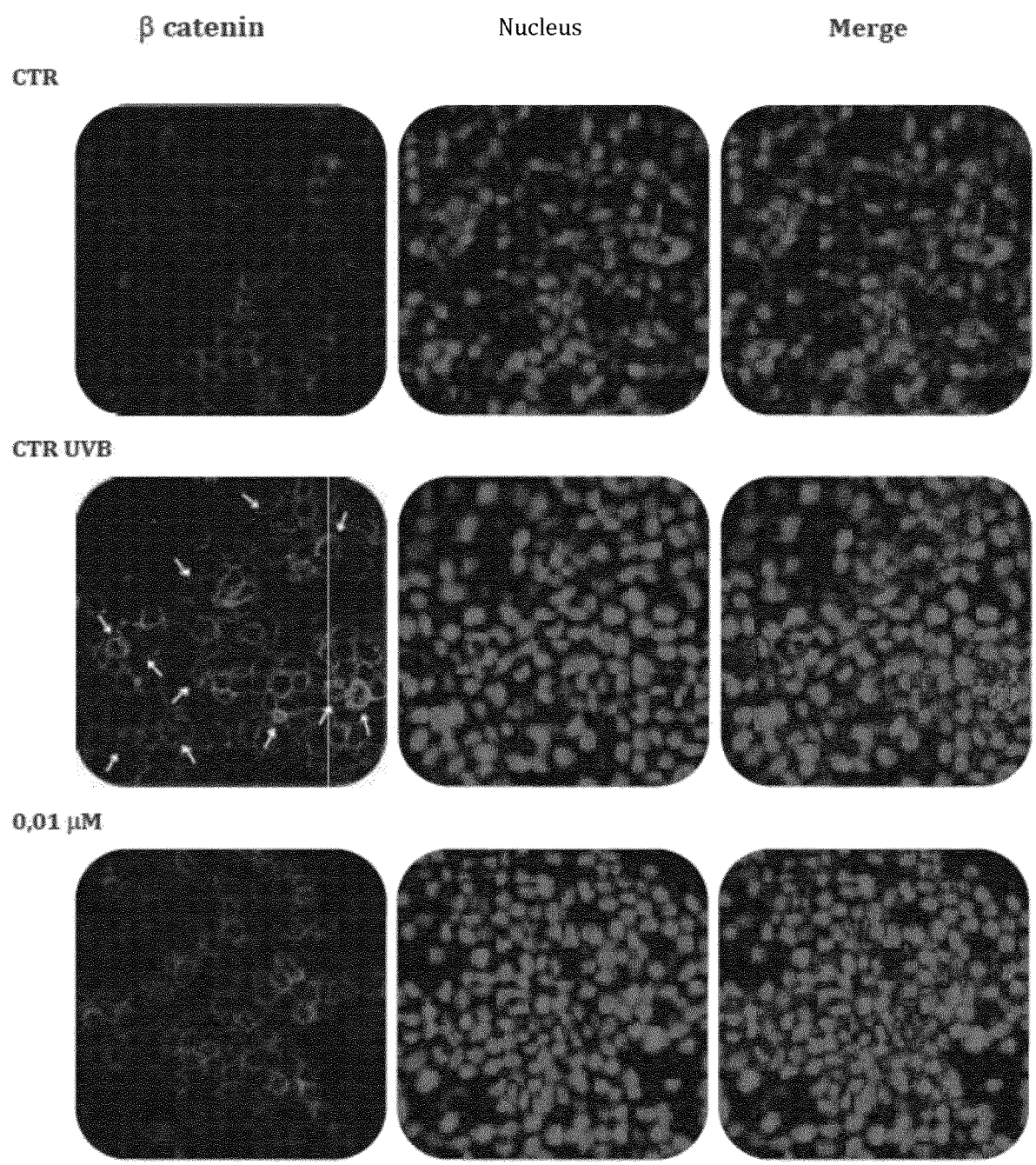
FIG. 3 shows the effect of *Salvia haenkei* 0.1 and 0.01. μM (SH01) on the translocation and expression of β catenin in HaCaT keratinocytes before (FIG. 3A) and after (FIG. 3B) exposure to UVB ultraviolet radiation 30 KJ/m2. Markings of β catenin (Alexa Fluor 488, λ etc=490 nm; λ emis=525 nm) and of the nuclei (propidium iodide λ max etc.=495 nm; λ emis=610 nm).
Figure 3B:
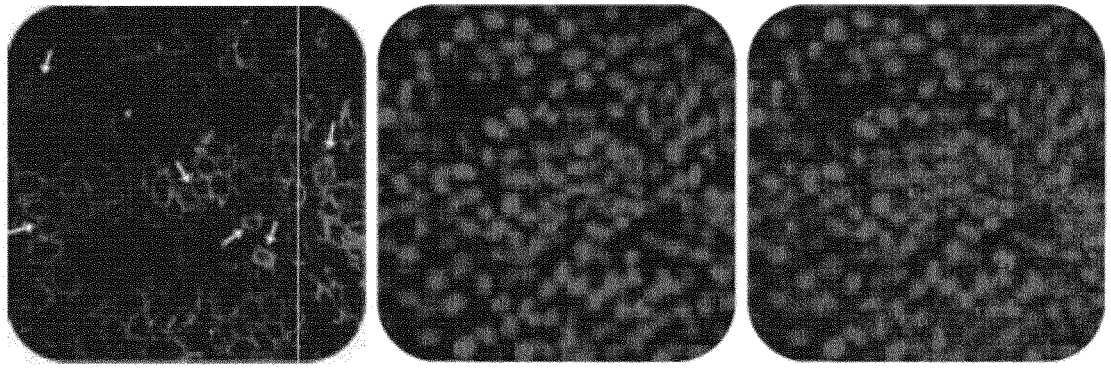
Figure 3B:
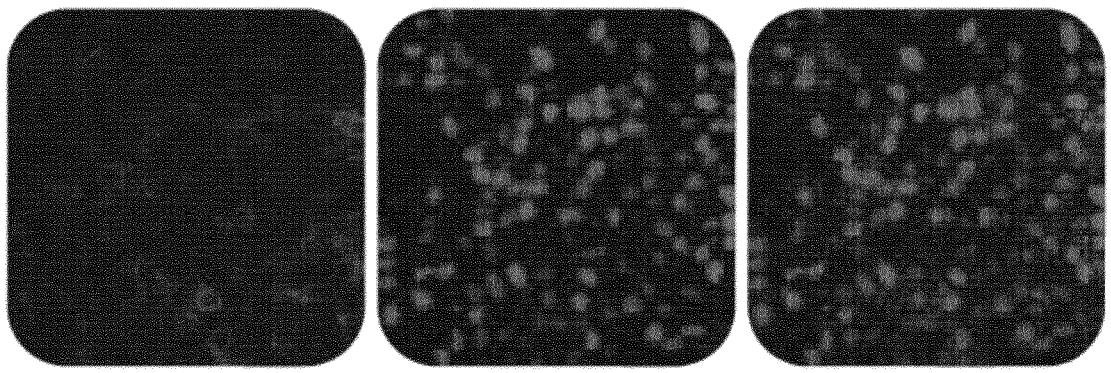
Figure 3B:
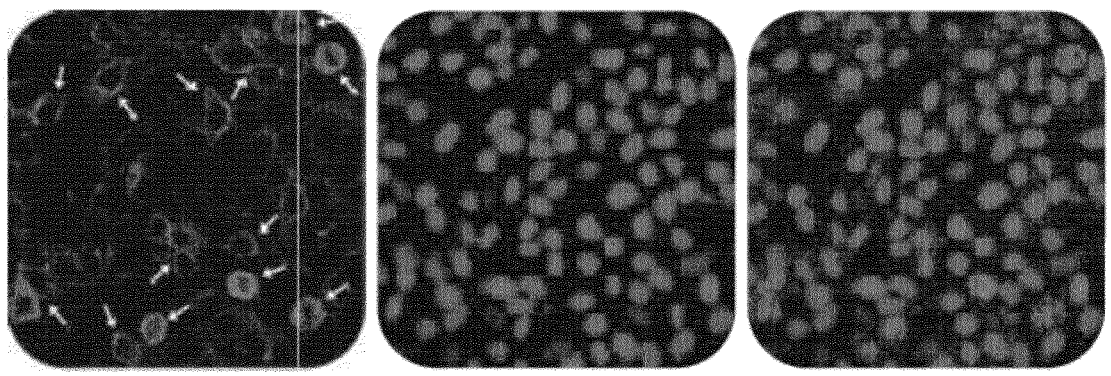

Through immunocytochemistry, it was evaluated the translocation of β catenin from the membrane, where it contributes to the maintenance of cell-cell adhesions for interaction with E-cadherin and fundamental for its functioning, to the nuclear-perinuclear zone following exposure to ultraviolet radiation (UVB 30 KJ/m$^2$) activating the important WNT pathway to ensure cell proliferation and differentiation, leading to the development of an invasive cellular phenotype. In FIGS. 3A and 3B, it is possible to observe the slides that have been set up with exposed cells and not with the UVB rays. It can be seen that, following exposure to ultraviolet radiation, β catenin begins to move from the membrane to the perinuclear zone. The extract does not seem to diminish this translocation, however, it seems that its expression in the presence of the SH01 treatment increases and reinforces the adhesions between the cells.

The invention claimed is:

1. A method of treating dermatological diseases, said method comprising
    administering to a subject in need thereof a *Salvia haenkei* extract as a re-epithelizing agent, and
    re-epithelizing tissues affected by said dermatological diseases, wherein said dermatological diseases are ichthyosis, excessive secretion of sebum, microbial infection, dermatophytosis, psoriasis, seborrheic dermatitis, dandruff, alopecia, allergic dermatosis, urticaria, scleroderma, contact dermatitis, atopic dermatitis, chronic actinic dermatitis or photodermatosis.

2. The method of claim 1, wherein said dermatological disease is ichthyosis.

3. The method of claim 1, wherein said dermatological disease is atopic dermatitis.

4. The method of claim 1, wherein said extract is to be administered via external topical route.

5. The method of claim 1, wherein said extract is to be administered via external topical route in a dose of 1-1,000 mg per day.

6. The method of claim 1, wherein the *Salvia haenkei* extract is in the form of a pharmaceutical composition further comprising pharmaceutically acceptable vehicles.

7. The method of claim 6, said pharmaceutical composition being administered via external topical route.

8. The method of claim 6, said pharmaceutical composition being in the form of ointment, lotion, cream, emulsion, paste, gel, aqueous solution, spray, patch, serum, soaked gauze, dressing, or a combination thereof.

9. The method of claim 6, said pharmaceutical composition comprising *Salvia haenkei* extract in a concentration of 0.1-500 mg/ml of said pharmaceutical composition.

10. The method of claim 6, said composition further comprising at least one active dermatological principle selected from anti-inflammatory agents, cortisonic agents, antibiotics, antihistaminic agents, anti-acne agents, anti-dandruff agents, anti-psoriasis agents, antifungal agents, antibacterial agents, anti-seborrheic agents, keratolytic agents, humectants, anti-free radical agents, antioxidants, vitamins, and mixtures thereof.

* * * * *